United States Patent [19]

Latorraca

[11] Patent Number: 5,368,019
[45] Date of Patent: Nov. 29, 1994

[54] SYSTEM AND METHOD FOR OPERATING A RESPIRATOR COMPRESSOR SYSTEM UNDER LOW VOLTAGE CONDITIONS

[75] Inventor: Gary Latorraca, San Diego, Calif.

[73] Assignee: Puritan-Bennett Corporation, Carlsbad, Calif.

[21] Appl. No.: 991,442

[22] Filed: Dec. 16, 1992

[51] Int. Cl.[5] .............................................. A61M 16/00
[52] U.S. Cl. ........................ 128/204.18; 128/204.21
[58] Field of Search ............... 128/204.18, 204.21, 128/204.23; 417/28, 29, 282, 44 A

[56] References Cited

U.S. PATENT DOCUMENTS

| | | | |
|---|---|---|---|
| 834,626 | 10/1906 | Longacre | 417/297 |
| 3,582,233 | 6/1971 | Bloom | 417/26 |
| 3,653,379 | 4/1972 | Glenn | 128/204.21 |
| 3,737,252 | 6/1973 | Pilarczyk et al. | 417/282 |
| 4,076,021 | 2/1978 | Thompson | 128/205.18 |
| 4,080,110 | 3/1978 | Szymaszek | 417/282 |
| 4,141,356 | 2/1979 | Smargiassi | 128/204.23 |
| 4,201,517 | 5/1980 | Ferguson | 417/12 |
| 4,210,136 | 7/1980 | Apple | 128/204.18 |
| 4,336,001 | 6/1982 | Andrew et al. | 417/282 |
| 4,401,413 | 8/1983 | Dickens | 417/26 |
| 4,405,290 | 9/1983 | Rannenberg | 417/282 |
| 4,412,788 | 11/1983 | Shaw et al. | 417/282 |
| 4,505,648 | 3/1985 | Heger et al. | 417/297 |
| 4,587,967 | 5/1986 | Chu et al. | 128/240.21 |
| 4,688,565 | 8/1987 | Kobayashi | 128/204.21 |
| 4,727,871 | 3/1988 | Smargiassi et al. | 128/204.17 |
| 4,819,123 | 4/1989 | Hatimaki | 417/26 |
| 4,838,257 | 6/1989 | Hatch | 128/204.18 |
| 4,886,056 | 12/1989 | Simpson | 128/201.25 |
| 4,899,740 | 2/1990 | Napolitano | 128/202.22 |
| 4,982,735 | 1/1991 | Yagata et al. | 128/204.23 |
| 5,038,770 | 8/1991 | Perkins | 128/204.18 |
| 5,237,987 | 8/1993 | Anderson et al. | 128/204.18 |

Primary Examiner—Edgar S. Burr
Assistant Examiner—Aaron J. Lewis
Attorney, Agent, or Firm—Fulwider Patton Lee & Utecht

[57] ABSTRACT

The system and method for operating an AC respirator compressor system at substantially subnormal line voltages includes a compressor, an accumulator, a solenoid unload or dump valve used to reduce the pressure at the outlet of the compressor, a check valve located downstream from the solenoid, a relief valve, a pressure sensor, and an AC voltage sensor. In a preferred embodiment, the compressor constantly supplies compressed air to the ventilator system, monitoring the accumulator pressure and activating the solenoid unload valve as required to maintain an acceptable range of pressure in the accumulator. In another preferred embodiment the compressor system can also be operated in an intermittent, or standby mode, to supply compressed air as needed. The respirator compressor system can maintain an acceptable range of pressure in the accumulator even during periods of low AC line voltage by monitoring both the accumulator pressure and the AC line supplying voltage to the respirator compressor system, and modulating the action of the solenoid unload valve to achieve low AC voltage operation.

6 Claims, 1 Drawing Sheet

SYSTEM AND METHOD FOR OPERATING A RESPIRATOR COMPRESSOR SYSTEM UNDER LOW VOLTAGE CONDITIONS

BACKGROUND OF THE INVENTION

1. Field of the Invention

This invention relates generally to the operation of a compressor system for supplying a respirator with pressurized breathing gas, and more specifically to the operation of a respirator compressor under low voltage conditions such as brownout.

2. Description of Related Art

Human respiration and ventilation systems of the type that are used for critical care in hospitals have become extraordinarily sophisticated as requirements for control of respiration have become better known. In particular, the modern respirator, which includes a computer control system for ventilating a patient during critical care periods, provides very sophisticated and controllable means to ventilate patients of various sizes and physiologies over a wide range of strategies related to the condition of the patient and the particular problems to be overcome. As such sophisticated respiration systems have become available, they have been more and more important in the ultimate recovery of a patient from traumatic events and surgery, and the interruption of their use under those circumstances is life threatening. The wide availability of such respirators has meant that they are now used throughout the world for critical care, exposing them to a wide variety of conditions in which unpredictable interruptions of electrical power are possible. For example, it has been known that rolling brown-outs can exist within metropolitan areas when a variety of conditions, including an unacceptable level of pollutants in the air or lack of full availability of fuel, diminish the ability to supply electrical power. Under such conditions, the auxiliary power of the hospital may not become active to restore full voltage. Accordingly, there remains a requirement for a viable and robust system to prevent the failure of a compressor to operate on demand during conditions of low voltage to the respirator. The present invention is a solution to this problem.

SUMMARY OF THE INVENTION

It is important that a respirator system includes a compressor system which is relatively robust and capable of continued operation under a variety of conditions. More specifically, it is highly desirable that the compressor system not be subject to interruption under less than optimal primary power supply conditions, particularly if the respirator is to be used in areas where changes in primary power supply parameters are possible. The present invention provides for a system and method for the operation of a compressor for a critical care respirator during conditions of lower than normal voltage from the primary power supply.

A gas supply system for a ventilator system commonly includes a gas compressor which is used for the purpose of providing compressed air for use by the ventilator. Ventilators of the type used in patient respirators must operate under a variety of conditions, including subnormal line voltages. A compressor system with the ability to operate under difficult power supply circumstances makes the entire respirator system more resilient to operating conditions. In circumstances where the ventilator is being used to ventilate a patient during critical care, it is clear that the stalling of a respirator compressor due to low voltage conditions, could potentially cause interruption of the ventilation process. Thus, the ability to provide a more resilient and adaptive compressor system supplying the ventilator is highly desirable.

In one mode of respirator operation, the respirator is connected to a supply of compressed gas external to the respirator. The compressor system then operates in an intermittent, or standby mode to replenish air in the accumulator which may have been depleted due to leaks or short term draws on the system. In a high duty cycle, or continuous mode, the respirator compressor operates more or less continuously in order to supply air to the accumulator which is drawn on directly by the respirator as a primary air source.

Briefly and in general terms, the present invention is embodied in a method and apparatus for operating an AC compressor system at substantially subnormal line voltages. The basic system includes the use of a compressor, a relief valve, a solenoid unload or dump valve used to reduce the pressure at the outlet of the compressor, an accumulator, a pressure sensor, and an AC voltage sensor. A check valve located downstream from the solenoid prevents high pressure air contained in the accumulator from providing back pressure to the output of the compressor. The respirator compressor system operates by compressing ambient air and delivering the air to the accumulator. Air is then drawn by the ventilator from the accumulator. During periods of low flow demand from the ventilator, excess pressure within the accumulator is vented through a pressure relief valve. Whenever the compressor motor is started, a solenoid is opened to relieve the pressure and allow the motor to reach full speed without operating against the high back pressure from the accumulator.

In the continuous or high duty cycle mode, the compressor preferably constantly supplies compressed air to the ventilator system, monitoring the accumulator pressure and activating the solenoid unload valve as required to maintain an acceptable minimum pressure in the accumulator, or alternatively to maintain a desired range of pressure in the accumulator.

When the respirator is in an intermittent or standby mode, the compressor system can also be operated when needed. Such a mode may be used to replenish pressure losses in the accumulator due to leaks or other low volume draws on the system. In such a mode, the respirator compressor system of the invention is not necessarily required for normal operation. However, under circumstances of low voltage supplied to the respirator compressor system, the respirator compressor system of the invention monitors the accumulator pressure, activates the compressor, and activates the solenoid unload valve as required to maintain an acceptable minimum or desired range of pressure in the accumulator.

The respirator compressor system of the invention is able to maintain an acceptable minimum pressure in the accumulator even during periods of low AC line voltage by monitoring both the accumulator pressure and the AC line supplying voltage to the respirator compressor system, and modulating the action of the solenoid unload valve to achieve low AC voltage operation. An accumulator pressure signal is provided as feedback to a control logic unit for control of the solenoid unload valve. For instance, the speed of an AC motor will decrease when there is low AC voltage available for power. By use of the respirator compressor of the invention and monitoring AC voltage supplied to the respirator compressor and accumulator pressure, the solenoid unload valve may be modulated to allow the motor to operate substantially below its normal stall voltage, thereby extending the useful voltage range over which the respirator compressor can operate.

Control logic of the type that may be used with the invention may be embodied in a digital logic circuit of the type that contains both a memory and internal clock circuit in combination with a modest central processor unit. Such a control logic unit may be programmed to accept the inputs from the line voltage sensor and pressure sensors to operate the compressor motor and the unload solenoid to prevent compressor stall at lower than nominal voltages. In practice, the control logic will be programmed to turn on the compressor motor when the line voltage is within the range that has been predetermined to allow compressor operation for usable pressures in the accumulator. The control logic will also modulate the unload solenoid valve to prevent motor stall due to back pressure on the compressor when the voltage is below that at which the compressor will operate against full accumulator pressure.

Thus, by use of the invention, the problems associated with compressor stall at low voltages can be avoided over a wider range of input power voltage than would otherwise be possible. Other features and advantages of the invention will become apparent from the following detailed description taken in conjunction with the accompanying drawings which illustrate, by way of example, the principles of the invention.

DETAILED DESCRIPTION OF THE PREFERRED EMBODIMENTS

Figure 1:
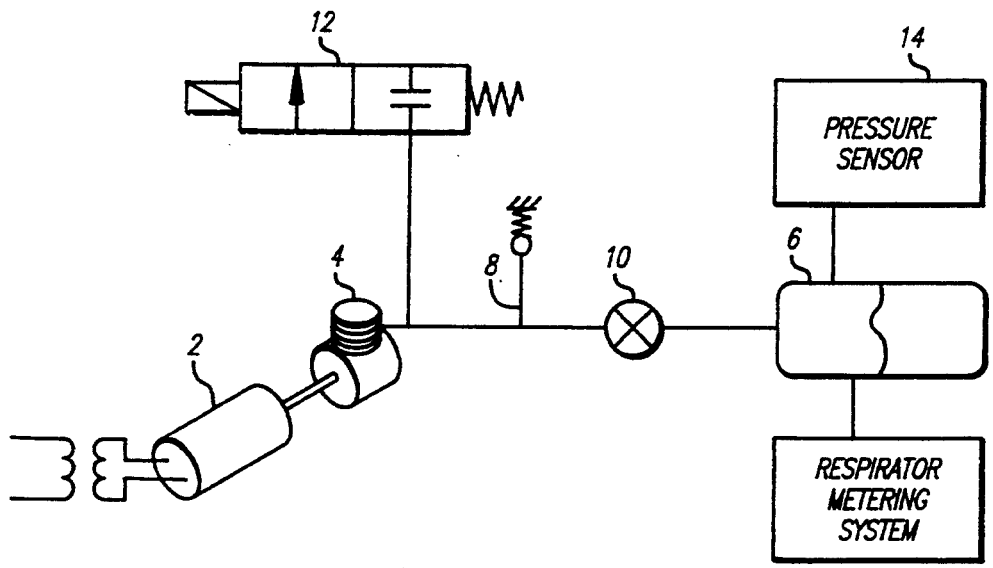
FIG. 1 is a compressor accumulator system of prior art respirator compression systems.

Patient respirators of the type used to ventilate a patient during periods of critical care include a compressor system driven by an electric motor which is connected to line current available throughout the hospital. The line current has an associated voltage, typically either 110 or 220 volts, depending upon the supply from the main power lines available. In the event that there is a power interruption, most hospitals and other critical care units have a provision for auxiliary power which will come on line and provide sufficient power to run all of the hospital appliances, including respirators. Under some circumstances, however, especially rolling brownouts of the type that have recently been instituted during periods of low power availability, it has become normal for the primary power source to be reduced in voltage without being actually discontinued. During such circumstances the auxiliary power system will not be actuated and the hospital appliances, including respirators, must operate with the reduced voltage power supplies. Under such circumstances, it is not unusual for the motor driving the compressor to be unable to overcome the load imposed by back pressure from the reservoir on the output of the compressor, since the motor torque is reduced due to lowered voltage. In the event that this were to occur, the compressor would not be able to stay on line until the pressure in the respirator reservoir is reduced to the point that respirator operation would be seriously affected.

The present invention provides a method and apparatus for operating an AC compressor system of the type used in a respirator at voltages substantially below those normally required. The system according to the invention includes an electric motor connected to the line voltage and mechanically driving a compressor. The output of the compressor is fed to a reservoir or accumulator via a check valve. The solenoid unload valve is controlled by control logic which senses the accumulator pressure and the AC line voltage to determine when the solenoid unload valve is to be opened to prevent compressor stall.

Under normal circumstances, the system operates to compress ambient air and deliver the air to an accumulator. The air is drawn from the accumulator by a system operating to ventilate a patient. During periods of low pneumatic demand by the ventilator, excess pressure within the accumulator may be vented through the pressure relief valve.

Under certain circumstances, the air compression system may be considered to be an auxiliary air supply and its operation is not always required. Thus, the system will be inoperative when compressed air is not called for by the operation of the ventilator. When the system is in such a standby mode, the control function monitors accumulator pressure and can activate the compressor as required to maintain an acceptable and desired internal pressure in the accumulator, thus maintaining a desired accumulator pressure even when leaks may occur somewhere within the system. In the method according to the invention, a solenoid unload valve operates to relieve pressure when the compressor motor is started, thus allowing the motor to reach full speed without operating against a significant load. A check valve downstream from the solenoid operates to prevent pressure in the accumulator from causing back pressure against the relief valve and compressor. A control unit monitors the accumulator pressure and the AC line voltage and modulates the solenoid unload valve to continue operation during low voltage AC supply. The control unit is preferably programmed to provide for continued compressor operation for combinations of pressure and AC line voltage which would otherwise cause motor stall by operating the solenoid unload valve to diminish back pressure on the compressor through modulation of the solenoid unload valve. By use of this method, the motor can be made to operate at substantially below its normal stall voltage, thereby extending the useful range over which the compressor can operate.

Referring to FIG. 1, a respirator compressor accumulator system of the prior art is illustrated in which a conventional electric motor 2 drives a compressor 4 with its output fed to an accumulator 6. A pressure relief valve 8 is configured to provide relief from excess pressure in the system. A check valve 10 is used to prevent back pressure from the accumulator from feeding back into the outlet line from the compressor. However, such a check valve does not prevent the output line to the compressor from immediately sensing the accumulator pressure upon start up. A solenoid unload valve 12 is connected for fluid communication with the accumulator for unloading the compressor at start up. A pressure sensor 14 is provided downstream of the compressor for monitoring the pressure available for supply to a respirator system.

Figure 2:
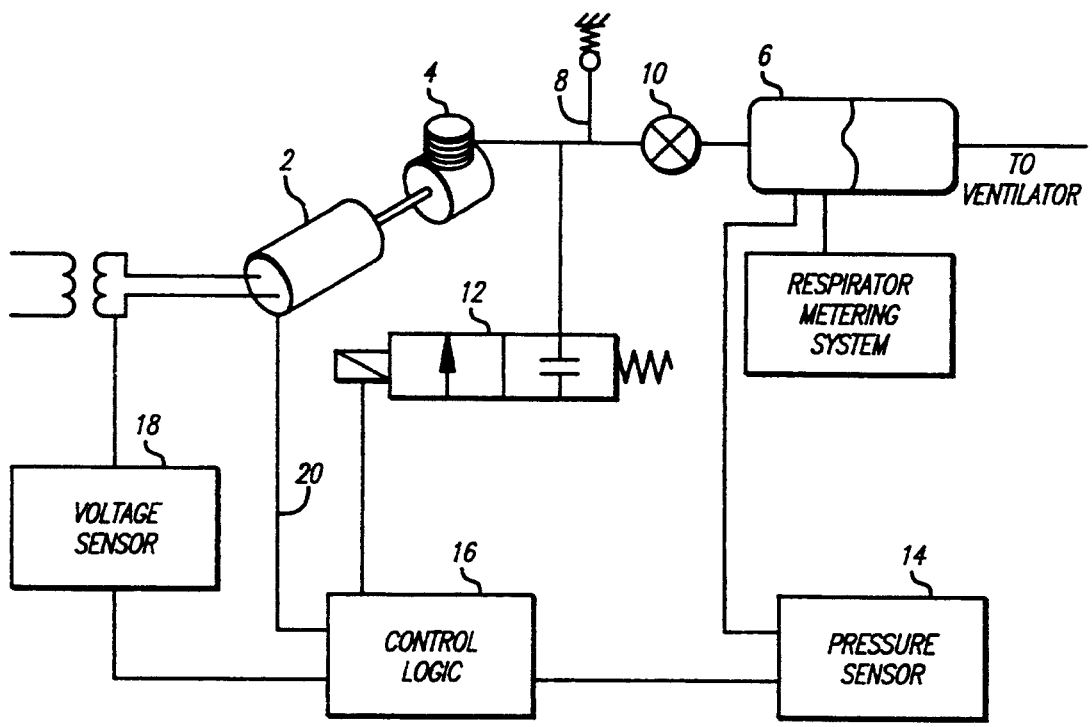
FIG. 2 is a block diagram of the present invention, illustrating the arrangement of the major components.

FIG. 2 illustrates the arrangement of the respirator compressor system of the present invention in which the motor 2 drives the compressor 4 to supply air to the accumulator 6 in a manner similar to that of the prior art. However, the respirator compressor of the invention involves the use of a pressure sensor 14 downstream of the accumulator to continuously provide an indication of system pressure to the control logic unit 16. This signal is utilized in the control logic unit along with a signal from an AC voltage sensor 18 representing the AC line voltage provided to the compressor, in order to provide a command signal to modulate the operation of the solenoid unload valve. Using this system, it has been found that the invention allows for continued operation with line voltages as low as 65% of nominal line voltage, while still maintaining a substantial pressure in the accumulator and allowing continued operation of the respirator.

In operation, it has been found that a Micro Switch pressure sensor, Model No. 240PC provides for an accurate indication of the pressure and outputs a voltage compatible for the control function. Similarly, it has been found that a Bellofram model 70BP back pressure regulator or Humphrey model 310 relief valve may be utilized as a system relief valve. The solenoid unload valve can be an ON-OFF valve that is solenoid activated, and is preferably upstream of the check valve. Such solenoid valves are widely commercially available. Alternatively, an Allied solenoid relief valve of the Wattmizer series has been found to be suitable for this application.

In a presently preferred embodiment, the accumulator is preferably formed from about 18 feet in length of 1 ¼" copper tubing, bent into a rectangular coil. In this preferred configuration, the accumulator can also function as a heat exchanger. The internal volume of the accumulator affects the amplitude of pressure variations for desired charging and discharging rates, so that the dimensions of the accumulator can be selected to control the desired maximum and minimum pressure levels in the respirator compressor. Alternatively, a sealed container, that is preferably rigid, may also be suitable for use as the accumulator.

In one preferred embodiment of the method of the invention for operating a respirator compressor at low voltage, the electrical motor preferably continuously drives a compressor to charge the accumulator. The output pressure of the accumulator and the AC line voltage to the motor are monitored, and electrical signals representing the output pressure of the accumulator and the AC line voltage are received by the logic control unit to provide a command signal to modulate the operation of the solenoid unload valve to lower the output pressure of the compressor, decreasing the voltage at which compressor stall will occur. The control logic unit activates the solenoid unload valve as required to maintain at least an acceptable minimum pressure in the accumulator. The solenoid unload valve may also be operated to maintain a desired pressure range in the accumulator.

In another preferred embodiment of the method of the invention, the compressor system is operated in an intermittent, or standby mode, when needed. In such a mode, which can be used to overcome decreases in pressure due to leaks or other low volume drains on the system, the compressor will operate with a short duty cycle to build pressure in the accumulator. If lower than normal voltage is supplied to the respirator compressor system, the respirator compressor system of the invention monitors the accumulator pressure, and activates the compressor motor. The compressor motor is electrically connected to the control logic unit by line 20 for control of the compressor motor in this standby mode and the control logic unit activates the solenoid unload valve as required to maintain an acceptable minimum pressure in the accumulator. The solenoid unload valve may also be operated to maintain a desired pressure range in the accumulator.

The Control unit of the invention may be of the type well known in the art in which a digital processor is used to control external electromechanical components based upon inputs from one or more sensors. In practice, such control units can comprise microprocessors which include internal clocks and random and fixed memories. The fixed, or read only memory(ROM) usually contains the operating logic for the microprocessor that governs its internal functions. The random access memory(RAM) is the memory that may be accessed by the microprocessor to store and retrieve information to be used to perform calculations. Alternatively, the control unit may comprise a programmable logic array and memory devices, or other logical elements, in combination with timing devices. The control unit of the invention receives inputs from a pressure sensor in communication with an accumulator and a voltage sensor in communication with the line voltage to be used by the compressor motor. The control unit then, based on the inputs from these sensors, controls the compressor motor and unload solenoid valve to prevent compressor stall at lower line voltages than would otherwise be possible. In a presently preferred embodiment, the control unit operates a cooling fan whenever the compressor motor is on and a condensate dump solenoid is opened for on-half (½) second every 10 minutes of operation. The program to operate the compressor motor and unload solenoid in a presently preferred embodiment is as follows:

---

MOTOR COMPRESSOR:

$M_i = 1$ IFF; ( ON/OFF $= 1$ OR RECHARGE$_i = 1$ )
-AND-
[ AC__LOW $= 1$ OR (AC__TOO__LOW $= 1$ AND $M_{i-1} = 1$ ) ]

RECHARGE$_i$ EQUALS 1 IF; $P_{15} = 0$
OR
( $P_{15} = 1$ AND RECHARGE$_{i-1} = 1$)
EQUALS 0 IF; $P_{25} = 1$

---

GLOSSARY

SUBSCRIPT 'i' REFERS TO THE CURRENT TIME INTERVAL
SUBSCRIPT 'i−1' REFERS TO THE PRECEDING TIME INTERVAL
(CIRCUITRY EXISTS TO ENSURE THAT TIME DEPENDENT VARIABLES ARE PROPERLY INITIALIZED AT STARTUP)
ON/OFF=SIGNAL FROM THE VENTILATOR; 0=OFF, 1=ON
AC__LOW=AC LINE MONITOR SIGNAL; $0 = < -20\%$, $1 \geq -20\%$ AC_TOO_LOW=AC LINE MONITOR SIGNAL; 0=<−35%, 1=≧−35%
$M_1$=COMPRESSOR MOTOR COMMAND; 0=OFF, 1=ON
$P_{15}$=PRESS XDUCER OUTPUT; 0=<15 PSIG, 1=≧15 PSIG
$P_{25}$=PRESS XDUCER OUTPUT; 0=<25 PSIG, 1=≧25 PSIG This program corresponds to the following logic:
1. In order to start the motor, the AC line voltage to the compressor motor must be no lower than 20% below the nominal line voltage.
2. If the line voltage is within 20% of nominal, the motor will be switched on if the ventilator system requests it.
3. If the line voltage is within 20% of nominal, but the ventilator does not request compressor operation, the motor will operate as required to maintain the accumulator pressure at a desired level.
4. If the motor is running and the voltage remains within 35% of nominal line voltage, the motor will stay on.

The Unload Solenoid logic is as follows:

---
UNLOAD SOLENOID:
$SOL_i = 1$ IFF;   ($M_i = 1$ AND $M_{i−n} = 0$)

OR

{(AC_LOW = 0 AND AC_TOO_LOW = 1)

AND

[ (IF PRESS_INC = 1 AND $P_{15}$ = 1)

OR (IF PRESS_INC = 0 AND $P_{10}$ = 1)}

---

GLOSSARY

SUBSCRIPT 'i' REFERS TO THE CURRENT TIME INTERVAL SUBSCRIPT 'i−n' REFERS TO AN EARLIER TIME INTERVAL. 'n' IS CHOSEN LARGE ENOUGH TO GIVE THE MOTOR TIME TO REACH FULL SPEED. (CIRCUITRY EXISTS TO ENSURE THAT TIME DEPENDENT VARIABLES ARE PROPERLY INITIALIZED AT STARTUP)
SOLi—CURRENT SOLENOID STATE; 0=OFF, 1=ON
AC_LOW=AC LINE MONITOR SIGNAL; 0=<20%, 1=≧−20%
AC_TOO_LOW=AC LINE MONITOR SIGNAL; 0=<−35%, 1=≧−35%
$M_1$=COMPRESSOR MOTOR COMMAND; 0=OFF, 1=ON
$P_{10}$=PRESS XDUCER OUTPUT; 0=<10 PSIG, 1=≧10 PSIG
$P_{15}$=PRESS XDUCER OUTPUT; 0=<15 PSIG, 1=≧15 PSIG
PRESS_INC=VARIABLE THAT INDICATES DIRECTION OF ACCUMULATOR PRESSURE CHANGE; 0=DECREASING, 1=INCREASING

This program corresponds to the following logic:

1. Whenever the motor is turned on, the unload solenoid is actuated and remains actuated until the motor reaches full speed.
2. When the line voltage is within the predetermined range of 65% to 80% of the nominal line voltage, the unload solenoid is modulated to keep the accumulator within a desired range, in this case between 10 and 15 PSIG.

While the above program has been found to be effective in a specific application, and for a specific ventilator design, those skilled in the art will recognize that programs for such a controller will probably have to be somewhat altered to allow for different parameters in other systems.

From the above description, it will be evident to those skilled in the art that the present invention substantially improves the ability of a compressor system to operate during periods of low line voltage. Furthermore, the system is capable of fully automatic operation with relatively simple inputs and based upon reliable components. While a particular form of the invention has been illustrated and described, it will also be apparent that various modifications can be made without departing from the spirit and scope of the invention. Accordingly, it is not intended that the invention be limited except as by the appended claims.

What is claimed is:

1. A method for operating a respirator compressor system at low voltage, said respirator compressor system including a rigid accumulator for temporarily storing gas within a desired pressure range for supplying the gas to a ventilator system, a gas compressor driven by an electric motor, said gas compressor having an inlet for gas to be compressed and an outlet for compressed gas in fluid communication with said accumulator, a solenoid unload valve connected in fluid communication with said outlet of said gas compressor for reducing the pressure at the outlet of the compressor, a pressure sensor for measuring gas pressure within said accumulator operative to generate an electrical signal indicating accumulator pressure, an AC voltage sensor for measuring voltage supplied to said electric drive motor of said gas compressor, and control logic means for controlling operation of said solenoid unload valve, comprising the steps of:

operating said gas compressor to charge said accumulator with pressurized gas;

measuring the gas pressure in the accumulator and generating an electrical gas pressure signal representing accumulator gas pressure;

measuring line voltage to the drive motor of the gas compressor, and generating an electrical line voltage signal representing said voltage;

providing a command signal to modulate the operation of the solenoid unload valve to lower the output pressure of the compressor responsive to said gas pressure signal and said line voltage signal, thus preventing compressor stall over a broader input voltage range than would otherwise be possible.

2. The method of claim 1, wherein the electrical respirator compressor system is operated at a reduced voltage as low as 65% of normal line voltage.

3. The method of claim 1, wherein the respirator compressor constantly supplies compressed air to the accumulator, and the electrical respirator compressor system maintains an acceptable pressure minimum in the accumulator even during periods of low voltage.

4. The method of claim 1, wherein the respirator compressor supplies compressed air to the respirator system in an intermittent or standby mode, and activates the compressor and activates the solenoid unload valve as required to maintain an acceptable minimum pressure in the accumulator during periods of low voltage.

5. A system for operating an electrical respirator compressor system at low voltage, comprising:

a rigid walled accumulator for temporarily storing gas within a desired pressure range for supplying the gas to a ventilator system;

a gas compressor having an electrical drive motor, and having an inlet for gas to be compressed and an outlet in fluid communication with said accumulator for supplying compressed gas at an output pressure to said accumulator;

a solenoid unload valve connected in fluid communication with said outlet of said gas compressor for reducing the pressure at the outlet of the compressor;

a relief valve for venting excess pressure from the accumulator;

a pressure sensor for measuring pressure within said accumulator operative to generate a signal indicating accumulator pressure;

a voltage sensor for measuring voltage supplied to said electrical drive motor of said gas compressor operative to generate a signal indicating the voltage supplied to said electrical drive motor; and control logic means connected to said pressure sensor and said voltage sensor for receiving said line voltage signal and said signal indicating accumulator pressure, said control logic means operative to generate a signal for control of the solenoid unload valve to lower the output pressure of the compressor responsive to said gas pressure signal and said line voltage signal, thus decreasing the voltage at which compressor stall will occur.

6. The system of claim 5, wherein a check valve is located in fluid communication with said solenoid unload valve and downstream from the solenoid unload valve to prevent high pressure air contained in the accumulator from providing back pressure to the gas compressor.

* * * * *